(12) United States Patent
Meyer et al.

(10) Patent No.: US 12,655,394 B2
(45) Date of Patent: Jun. 16, 2026

(54) OVARIAN CANCER ORGANOID CULTURE

(71) Applicant: MAX-PLANCK-GESELLSCHAFT ZUR FÖRDERUNG DER WISSENSCHAFTEN E.V., Munich (DE)

(72) Inventors: Thomas F. Meyer, Falkensee (DE); Mirjana Kessler, Berlin (DE)

(73) Assignee: MAX-PLANCK-GESELLSCHAFT ZUR FÖRDERUNG DER WISSENSCHAFTEN E.V., Munich (DE)

( * ) Notice: Subject to any disclaimer, the term of this patent is extended or adjusted under 35 U.S.C. 154(b) by 856 days.

(21) Appl. No.: 16/967,548

(22) PCT Filed: Feb. 22, 2019

(86) PCT No.: PCT/EP2019/054468
§ 371 (c)(1),
(2) Date: Aug. 5, 2020

(87) PCT Pub. No.: WO2019/162453
PCT Pub. Date: Aug. 29, 2019

(65) Prior Publication Data
US 2021/0230555 A1      Jul. 29, 2021

(30) Foreign Application Priority Data

Feb. 23, 2018      (EP) ..................................... 18158377

(51) Int. Cl.
*C12N 5/09*          (2010.01)
(52) U.S. Cl.
CPC ........ *C12N 5/0693* (2013.01); *C12N 2501/11* (2013.01); *C12N 2501/155* (2013.01); *C12N 2501/415* (2013.01); *C12N 2501/727* (2013.01); *C12N 2503/02* (2013.01); *C12N 2511/00* (2013.01)
(58) Field of Classification Search
CPC .............. C12N 5/0693; C12N 2501/11; C12N 2501/155; C12N 2501/415; C12N 2501/727; C12N 2503/02; C12N 2511/00; G01N 2800/101; G01N 33/5011
See application file for complete search history.

(56) References Cited

U.S. PATENT DOCUMENTS

2012/0028355 A1      2/2012  Sato et al.
2012/0196312 A1      8/2012  Sato
2016/0237400 A1*     8/2016  Xian ...................... A61K 35/30

OTHER PUBLICATIONS

Jabs et al, Molecular systems biology, 13: 955, 2017. (Year: 2017).*
Jabs et al (Mol Syst Biol. (2017) 13: 955) (Year: 2017).*

Noll et al (Nature Medicine, vol. 22, No. 3, Mar. 2016). (Year: 2016).*
Schindler, Adam J., Arisa Watanabe, and Stephen B. Howell. "LGR5 and LGR6 in stem cell biology and ovarian cancer." Oncotarget 9.1 (2018): 1346. (Year: 2018).*
McLean, Karen, et al. "Human ovarian carcinoma-associated mesenchymal stem cells regulate cancer stem cells and tumorigenesis via altered BMP production." The Journal of clinical investigation 121.8 (2011): 3206-3219. (Year: 2011).*
TCGA study, "Integrated genomic analyses of ovarian carcinoma", Nature vol. 474, 2011, pp. 609-615.
Barker et al., "Identification of stem cells in small intestine and colon by marker gene Lgr5", Nature vol. 449, 2007, pp. 1003-1007.
Shaw et al., "Candidate serous cancer precursors in fallopian tube epithelium of BRCA1/2 mutation carriers", Modern Pathology 22, 2009, pp. 1133-1138.
McLean et al., "Human ovarian carcinoma-associated mesenchymal stem cells regulate cancer stem cells and tumorigenesis via altered BMP production", The Journal of Clinical Investigation, vol. 121, No. 8, 2011, pp. 3206-3219.
Hoffmann et al., "Stable expansion of high-grade serous ovarian cancer organoids requires a low-Wnt environment", The EMBO Journal, 39, e104013, 2020, 23 pages.
Jabs et al., "Screening drug effects in patient-derived cancer cells links organoid responses to genome alterations", Molecular Systems Biology, vol. 13. 955, Nov. 27, 2017, 16 pages, XP055496120.
Noll et al., "CYP3A5 mediates basal and acquired therapy resistance in different subtypes of pancreatic ductal adenocarcinoma", Nature Medicine, vol. 22, No. 3, Feb. 8, 2016, pp. 278-287, XP055496124.
Coffman et al., "Human carcinoma-associated mesenchymal stem cells promote ovarian cancer chemotherapy resistance via a BMP4/HH signaling loop", Oncotarget, vol. 7, No. 6, Jan. 9, 2016. pp. 6916-6932, XP055496128.
Peng et al., "The BMP Signaling Pathway Leads to Enhanced Proliferation in Serous Ovarian Cancer—A Potential Therapeutic Target", Molecular Carcinogenesis, vol. 55, Feb. 7, 2015, pp. 335-345, XP055496129.
Kessler et al., "The Notich and Wnt pathways regulate sternness and differentiation in human fallopian tube organoids", Nature Communications, vol. 6, 8989, Dec. 8, 2015, 11 pages, XP055496132.
Fujii et al., "A Colorectal Tumor Organoid Library Demonstrates Progressive Loss of Niche Factor Requirements during Tumorigenesis", Cell Stem Cell, vol. 18, No. 6, Jun. 2, 2016, pp. 827-838, XP029567586.

(Continued)

*Primary Examiner* — Anoop K Singh
*Assistant Examiner* — Constantina E Stavrou
(74) *Attorney, Agent, or Firm* — Rothwell, Figg, Ernst & Manbeck, P.C.

(57) ABSTRACT

The present invention relates to a method for the production of a culture, e.g. an organoid culture of ovarian cancer or cancer precursor cells, particularly of high grade serous ovarian carcinoma cells. By means of this method, an organoid culture of ovarian cancer or cancer precursor cells and a biobank comprising a plurality of different organoid cultures of ovarian cancer or cancer precursor cells may be generated. Further, a culture medium suitable for the long-term culture of ovarian cancer or cancer precursor cells is provided. Furthermore, use of the organoid culture and the biobank for medical applications, e.g. in the field of diagnostics, and therapy and in the field of drug screening is described.

9 Claims, 5 Drawing Sheets

(56) References Cited

OTHER PUBLICATIONS

Figure 1:
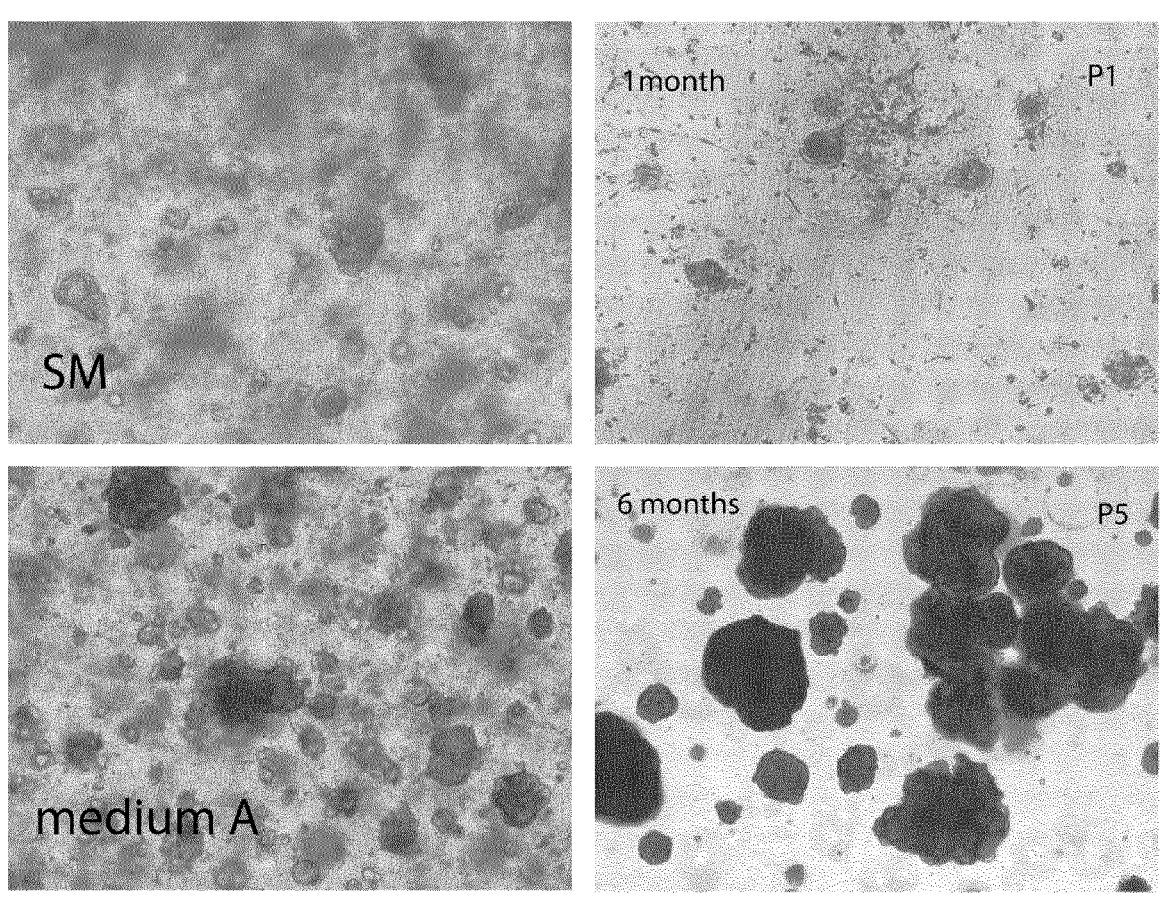

Van De Wetering et al., "Prospective Derivation of a Living Organoid Biobank of Colorectal Cancer Patients", Cell, vol. 161, No. 4, May 7, 2015, pp. 933-945, XP029224300.

International Search Report cited in PCT/2019/054468 dated Apr. 26, 2019, 3 pages.

Kopper et al. (2019) "An organoid platform for ovarian cancer captures intra- and interpatient heterogeneity" Nature Medicine 25:838-49.

Hoffmann et al. (2020) "Stable expansion of high-grade serous ovarian cancer organoids requires a low-Wnt environment" EMBO J. 39:e104013.

Nanki et al. (2020) "Patient-derived ovarian cancer organoids capture the genomic profiles of primary tumours applicable for drug sensitivity and resistance testing" Scientific Reports 10:12581.

* cited by examiner

ORG_1

ORG_2

OVARIAN CANCER ORGANOID CULTURE

CROSS REFERENCE TO RELATED APPLICATION

This application is a 35 U.S.C. 371 National Phase Entry Application from PCT/EP2019/054468, filed Feb. 22, 2019, which claims the benefit of European Patent Application No. 18158377.4 filed on Feb. 23, 2018, the disclosures of which are incorporated herein in their entirety by reference.

The present invention relates to a method for the production of a culture, e.g. an organoid culture of ovarian cancer or cancer precursor cells, particularly of high grade serous ovarian carcinoma cells. By means of this method, an organoid culture of ovarian cancer or cancer precursor cells and a biobank comprising a plurality of different organoid cultures of ovarian cancer or cancer precursor cells may be generated. Further, a culture medium suitable for the long-term culture of ovarian cancer or cancer precursor cells is provided. Furthermore, use of the organoid culture and the biobank for medical applications, e.g. in the field of diagnostics, and therapy and in the field of drug screening is described.

High grade serous ovarian cancer, the deadliest gynecological malignancy, with a 10 year survival rate of 30% remains a considerable challenge for clinicians who have only limited treatment options. Although initial response rate to standard platinum based chemotherapy is high (around 80 percent), almost all patients eventually relapse. Thus, despite some improvements in the lines of therapy, surgical debulking remains by far the most reliable determining factor of the long term outcome.

Due to the absence of suitable diagnostic tools which would improve detection rate at an early stage of the disease, and thereby improve prognosis, the development of new treatment options is hampered by the great genetic heterogeneity of this tumor type. While the vast majority of cases of high grade serous ovarian cancer harbors a mutation in the p53 gene (approx. 96%) all other somatic mutations in driver genes (PTEN, BRCA, Rb, NF etc) are found to exhibit relatively low prevalance. On the other hand, the genome of ovarian cancer cells is abundant with genomic rearrangements, amplifications and deletions as well as changes in the epigenetic regulation (TCGA study 2011, Nature 474, 609-615). Thus, it has been extremely difficult to classify patients into distinct subgroups solely based on the analysis of sequencing data, e.g. data obtained by next generation sequencing (NGS).

Also, so far it has been impossible to generate patient derived primary cultures with sufficient efficiency, as tumor isolates undergo senescence and growth arrest in vitro in standard cell culture systems. Therefore all current biobanks of ovarian cancer samples are comprised of "non viable" material, e.g. frozen tissue and paraffine blocks.

Adult stem cells have been identified in the epithelial surfaces of the body (Barker et al. 2007, Nature 449, 1003-1007). These cells can be propagated indefinitely in vitro in a long term 3D organoid culture within a Matrigel matrix give rise to continuously differentiating progeny (US 2012/0028355). Recently, our research group has established in vitro conditions for successful cultivation of human fallopian tube organoids, which provided framework for new concepts to study biology of the oviduct (Kessler et al 2015, Nature Communications 6, Article number: 8989). Despite minor differences in quantities of the individual components of the culture, the general principle for growing fallopian tube organoids resembles niche requirements from the gastrointestinal tract: Exogenous supplementation of Wnt pathway agonists Wnt and Rspondin, EGF and FGF10 as well as inhibition of the BMP signaling by Noggin.

BMPs belong to the superfamily of TGF-beta proteins, and are involved in regulation of broad range of developmental processes, lineage specification and differentiation. Inhibition of BMP pathway, via noggin is of essential importance for the maintenance of adult stem cells from healthy epithelia in in vitro culture.

R-spondins (e.g RSPO1) are potent amplifiers of Wnt signal which interact specifically with Lgr4-5-6 receptors, main determinants of stemness in adult tissues.

Effective inhibition of BMP signaling is also essential for the cultivation of colon cancer organoids, currently the best characterized organoid culture from patient derived tumor material (Van de Wetering et al. 2015, Cell 161, 933-945). Since more than 90% of colon cancers harbor mutations which lead to constitutive activation of Wnt pathway, colon cancer tumor organoids do not require exogenous Wnt3A supplementation, although Rspondin1 is still added to the medium. A systematic follow-up analysis revealed that at later stages of colon cancer progression an additional relaxation of niche requirements for organoid growth occurs but changes are highly patient dependent and diverse (Fujii et al 2016, Cell Stem Cell 18, 827-838).

For gynecological malignancies, the generation of a stable long-term cultivation model for solid tumor deposits has been challenging. Specific features of ovarian cancer, such as relative inaccessibility for exploratory imaging techniques and lack of knowledge about exact mechanism of early transformation in particular in comparison to intensely studied transition of polyps into colorectal cancer, have represented an objective hurdle in the development of advanced cell culture models.

The present inventors have now provided a method for producing an ovarian cancer cell organoid culture, particularly a human ovarian cancer cell organoid culture, more particularly from primary patient-derived ovarian cancer cells. This method allows production of stable organoid cultures which closely resemble in mutational profile or/and cellular phenotype to the parental cancer tissue. Contrary to healthy epithelium, the ovarian cancer cell organoid cultures do not need the inhibition of BMP signaling by antagonists, but even benefit form BMP signaling. Ovarian cancer organoids also do not require exogenous Wnt, e.g. Wnt 3a supplementation. Some patient isolates, however, were found to benefit from the presence of Rspondin.

Thus, a first aspect of the invention relates to a method for the production of an ovarian cancer or cancer precursor cell culture, e.g. a cancer or cancer precursor cell organoid culture. As a starting material, ovarian cancer or cancer precursor cells, particularly primary ovarian cancer or cancer precursor cells may be used. Ovarian cancer cells include cells from solid tumor deposits, ascites (fluid from the peritoneum) and circulating tumor cells present in blood. Cancer precursor cells include cells from premalignant lesions e.g. lesions in the fallopian tube, which already contain a mutation in at least one driver gene, such as p53, PTEN, BRCA, RB or/and NF. The ovarian cancer or cancer precursor cells may be derived from any mammalian species, e.g. human or other primates or rodents such as mouse or rat. More particularly, primary ovarian cancer or cancer precursor cells derived from human patients are used as a starting material. Surprisingly it was found that cancer cells as well as cancer precursor cells have altered niche requirements for cultivation in comparison to healthy tissue.

According to the invention, all cell culture systems may be used which are supportive of maintenance of stem cells such as feeders based cultures, low attachment systems, air liquid interface etc. Thus, the method may comprise a two-dimensional cell culture and in particular a three-dimensional cell culture, wherein an organoid culture may be produced.

The cultivation is carried out in a cell culture medium which is capable of BMP signaling, e.g. in a medium which comprises at least one compound which stimulates BMP signaling or/and which is essentially free of a compound which inhibits BMP signaling.

In the present invention, the culture medium can contain at least one compound which stimulates Wnt signaling, e.g. via Rspondin 1 (RSPO1). In particular, the culture medium can contain at least one compound which stimulates an Lgr4-6 receptor, e.g. via Rspondin 1.

A further aspect of the invention is an ovarian cancer or cancer precursor cell organoid culture. This culture is defined by the presence of ovarian cancer or cancer precursor cells in the form of organoids which may have an average size of about 200-500 μm. The cancer or cancer precursor cells are preferably characterized by the presence of cellular markers such as nuclear p53, EpCAM or/and PAX8, as well as a high proliferation index (as indicated e.g. by Ki-67 positive cells). In contrast to the polarized epithelial monolayer of cells from a healthy fallopian tube, ovarian cancer or cancer precursor organoids lack a central cavity, which is a consequence of loss of tissue architecture. A high degree of phenotypic similarity between generated organoid lines and parental tissues has been confirmed by comparison of standard set of markers as well as histological features.

The organoid culture is a stable culture, i.e. it can be propagated for a time of at least six months or longer in a suitable cell culture medium as described herein. The organoid culture may be subjected to freezing/thawing procedures, and expansion e.g. into a multi-well format, suitable for high throughput set ups and drug testing. If desired, cells of the organoid culture may be subjected to genetic modification, e.g. by genome editing.

A further aspect of the invention is a biobank comprising a plurality of different organoid cultures. The biobank may comprise the organoid cultures in the form of individual propagating organoid cultures or/and frozen organoid cultures.

A still further aspect of the invention relates to the use of a cell culture medium for the production of an organoid culture from ovarian cancer or cancer precursor cells. The cell culture medium may be selected from any suitable eukaryotic cell culture medium comprising salts, vitamins and trace elements. Preferably, the cell culture medium is supplemented with HEPES, glutamine, transferrin or/and insulin and optionally with albumin or/and serum such as fetal calf serum. Further, suitable supplements include, for example, a B27 supplement, nicotine amide, a Rock inhibitor such as a Y-27632, an N-2 supplement, and a TGF beta inhibitor such as SB-431542. For example, a suitable eukaryotic cell culture medium may be the Advanced DMEM/F12 medium (Gibco®) optionally supplemented as indicated above.

The medium can be used for long term in vitro expansion and differentiation of ovarian cancer cells or/and cancer precursors. all cell culture systems may be used which are supportive of maintenance of stem cells such as feeders based cultures, low attachment systems, air liquid interface etc.

The cell culture medium is capable of BMP signaling. This may be achieved by adding mitogenic growth factors capable of stimulating bone morphogenetic protein (BMP) signaling such as epidermal growth factor (EGF), fibroblast growth factor (FGF) and/or a Rspondin, such as Rspondin 1, e.g. human Rspondin 1 (UniProt Q2MKA7). Preferably, exogenous BMP, such as BMP2, e.g. human BMP2 (RefSeq NP_001191) is added to the medium. Further, it is preferred that inhibitors of BMP signaling, such as Noggin, a.g. human Noggin (RefSeq NP_005441) are omitted from the medium, i.e. not provided exogenously to the medium. Further, it is preferred that Wnt proteins such as Wnt 3a, e.g. human Wnt 3a (RefSeq NP_149122) are omitted from the medium, i.e. are not provided exogenously to the medium.

Two specific examples of suitable culture media are (i) a medium supplemented with BMP2, e.g. in a concentration of about 1-50 ng/ml, particularly about 5-20 ng/ml and more particularly of about 10 ng/ml, and EGF, e.g. in a concentration of about 1-200 ng/ml, particularly about 10-100 ng/ml, and more particularly of about 10 ng/ml, and (ii) a medium supplemented with EGF as indicated above, FGF, e.g. in a concentration of about 20-500 ng/ml, particularly about 50-200 ng/ml and more particularly of about 100 ng/ml, and Rspondin 1, e.g. in a concentration of about 50-100 ng/ml, particularly of about 100-700 ng/ml, or for example as 10% of a conditioned medium, harvested from the cell line producing the protein.

In addition to the above-mentioned components, the cell culture medium of the organoid culture may also comprise a suitable 3D cell culture matrix supporting the growth of organoids such as a basement membrane-like matrix, e.g. a Matrigel®, BME® or EHS® matrix. By embedding in a suitable matrix such as Matrigel and providing a suitable composition of paracrine niche factors in the medium, stem cells from the primary isolate will expand and differentiate into compact structures, i.e. cancer organoids, which can grow indefinitely.

In a particular embodiment, establishment of the organoid culture may involve two parallel cultivation set-ups, one without Rspondin supplementation and one with Rspondin supplementation. For example, one set-up may be carried out with a medium comprising EGF as mitogenic signal and BMP2 together with general organoid culture supplements as additional support and the other one with a medium which includes FGF and Rspondin supplementation.

Still a further aspect of the present invention relates to the use of the ovarian cancer or cancer precursor cell organoid culture or/and the biobank for medical applications, and drug screening. For example, the use may comprise determining the efficacy of a therapeutic compound in the treatment of ovarian cancer, e.g. for personalized medicine, or/and for the identification of a therapeutic compound suitable in the treatment of ovarian cancer, e.g. for drug screening.

Another example for a medical application is the use of the ovarian cancer or cancer precursor cell organoid culture or/and the biobank as a test system for cancer immunotherapy, e.g. for testing the efficacy of immune cells, e.g. T cells, in cancer immunotherapy, e.g. the testing of immune cells, e.g. T cells, obtained from the patient to be treated or obtained from a heterologous source, e.g. by determining antigen-specific immune responses, or for identifying novel neoantigens.

Furthermore, the present invention provides a therapeutic compound suitable for the treatment of an individual specimen of ovarian cancer, e.g. a specimen of ovarian cancer from an individual patient wherein efficacy of the compound has been tested against an organoid culture, particularly against an organoid culture of ovarian cancer or cancer precursor cells derived from said individual patient. Thus, the compound may be used for the treatment of ovarian cancer in a patient from which an ovarian cancer or cancer precursor cell organoid culture has been generated and tested with at least one therapeutic compound. In some embodiments, the patient is a chemotherapy naïve patient, particularly a patient who has been previously subjected to debulking surgery.

The features of the embodiments described herein can be combined independently of each other. In preferred embodiments, the present invention is defined by the following items:

1. A method for the production of an ovarian cancer or cancer precursor cell culture, e.g. from primary cancer cells including cells from tumor tissue and circulating tumor cancer cells, or from primary cancer precursor cells including cells from the fallopian tube, which harbor cancer driving mutations, said method comprising the steps:
   (a) cultivating ovarian cancer or cancer precursor cells in a suitable cell culture medium which is capable of BMP signaling.
   (b) optionally obtaining a cell culture from the cultivation step (a).

2. The method of item 1, wherein the cell culture is an organoid culture.

3. The method of item 1 or 2, wherein the culture medium comprises at least one compound which stimulates BMP signaling selected from mitogenic growth factors such as EGF or/and FGF, a BMP, e.g. BMP2, or/and a Rspondin, e.g. Rspondin1, wherein the medium particularly comprises
   (i) EGF or/and a BMP
   (ii) EGF, FGF or/and a Rspondin.

4. The method of any one of items 1 to 3, wherein the culture medium is free from exogenously added Wnt protein, e.g. from an exogenously added Wnt3a protein.

5. The method of any one of items 1 to 4, wherein the culture medium is free of an exogenously added compound which inhibits BMP signaling, such as Noggin.

6. The method of any one of the items 1 to 5, wherein the culture medium comprises at least one compound selected from the group consisting of a B27 supplement, nicotine amide, a Rock inhibitor such as Y-27632, an N-2 supplement, and a TGF beta inhibitor such as SB-431542.

7. The method of any one of the items 1 to 6, wherein the ovarian cancer or cancer precursor cells are primary ovarian cancer or cancer precursor cells, more particularly primary ovarian cancer or cancer precursor cells derived from a human patient.

8. The method of any one of the items 1 to 7, further comprising the step of determination of
   (i) the cellular phenotype,
   (ii) the mutational profile, or/and
   (iii) protein expression profile
   of (a) the ovarian cancer or cancer precursor cells, or/and (b) the culture, e.g. the organoid culture.

9. The method of any one of the items 1 to 8, wherein the ovarian cancer is a high-grade serous ovarian carcinoma.

10. An ovarian cancer or cancer precursor cell organoid culture which can be stably propagated.

11. The organoid culture of item 10, as obtainable by the method of any one of the items 1 to 9.

12. A biobank, comprising a plurality of different organoid cultures of item 10 or 11.

13. Use of an organoid culture of item 10 or 11, or a biobank of item 12, for the determination of the efficacy of a compound in the treatment of ovarian cancer.

14. Use of an organoid culture of item 10 or 11, or of a biobank of item 12, for the identification of a compound suitable in the treatment of ovarian cancer.

15. Use of a cell culture medium which is capable of BMP signaling, for the production of a culture from ovarian cancer or cancer precursor cells.

16. The use of item 15 for the production of an organoid culture.

17. The use of item 15 or 16, wherein the cell culture medium comprises at least one compound which stimulates BMP signaling selected from mitogenic growth factors such as EGF, FGF, a BMP, e.g. BMP2, or/and a Rspondin, e.g. Rspondin1, wherein the medium particularly comprises
   (i) EGF or/and BMP2, or
   (ii) EGF, FGF or/and a Rspondin.

18. The use of any one of items 15 to 17, wherein the ovarian cancer cells are primary ovarian cancer or cancer precursor cells, more particularly primary ovarian cancer or cancer precursor cells derived from a human patient.

19. The use of any one of items 15 to 18, wherein the culture medium is free from exogenously added Wnt protein, e.g. from an exogenously added Wnt3a protein.

20. The use of any one of items 15 to 19, wherein the cell culture medium is free of an exogenously added compound which inhibits BMP signaling, such as Noggin.

21. The use of any one of the items 15 to 20, wherein the cell culture medium comprises at least one compound selected from the group consisting of a B27 supplement, nicotine amide, a ROCK inhibitor such as Y-27632, an N-2 supplement, and a TGF beta inhibitor such as SB-431542.

22. A method for the determination of the efficacy of a compound in the treatment of ovarian cancer, particularly of ovarian cancer in an individual patient, comprising the steps
   (a) providing an ovarian cancer or cancer precursor cell organoid culture,
   (b) contacting at least one compound with the organoid culture provided in step (a), said at least one compound being selected from therapeutically active agents suitable for the treatment of ovarian cancer,
   (c) determining growth or/and propagation of the organoid culture after being contacted with the at least one compound, and
   (d) selecting at least one compound which inhibits growth or/and propagation of the organoid culture, as determined in step (c).

23. The method of item 22, wherein the organoid culture is as defined in item 10 or 11, or obtained from a biobank of item 12.

24. The method of any one of the items 22 to 23, wherein the organoid culture has been produced from a patient-derived sample of the ovarian cancer or cancer precursor cells from an individual patient to be treated.

25. The method of any one of the items 22 to 24, wherein the at least one compound in step (b) is selected from the group consisting of chemotherapeutic platinum compounds such as cis-platin, carboplatin or oxaliplatin.

26. A screening method for the identification of a compound suitable in the treatment of ovarian cancer, particularly of ovarian cancer in a plurality of different patients, comprising the steps
  (a) providing at least one ovarian cancer or cancer precursor cell organoid culture,
  (b) contacting at least one compound with the at least one organoid culture provided in step (a), said at least one compound being selected from candidate active agents presumed to be suitable for the treatment of ovarian cancer,
  (c) determining growth or/and propagation of the at least one organoid culture after being contacted with the at least one compound, and
  (d) selecting at least one compound which inhibits growth or/and propagation of at least one organoid culture, as determined in step (c).

27. The method of item 26, wherein the organoid culture is as defined in item 10 or 11, or obtained from a biobank of item 12.

28. The method of any one of the items 26 to 27, wherein a plurality of organoid cultures, obtained from different ovarian cancer or cancer precursor cells, particularly from a plurality of different patients, is analyzed.

29. A compound selected from active agents suitable for the treatment of ovarian cancer, for use in the treatment of a patient suffering from ovarian cancer, said treatment comprising the steps.
  (a) providing an ovarian cancer or cancer precursor cell organoid culture from said patient,
  (b) contacting at least one compound with the organoid culture provided in step (a), said at least one compound being selected from active agents suitable for the treatment of ovarian cancer,
  (c) determining growth or/and propagation of the organoid after being contacted with the at least one compound,
  (d) selecting a compound which inhibits growth or/and propagation of the organoid culture, as determined in step (c), and
  (e) treating the patient with compound selected in step (d).

30. The compound for use of item 29, wherein the organoid is obtained by the method of any one of the items 1 to 9.

31. The compound for use of item 29 or 30, wherein the organoid culture is an organoid culture as defined in item 10 or 11, or obtained from a biobank of item 12.

32. The compound for use of any one of the items 29 to 31, wherein the organoid culture is produced from a sample of the ovarian cancer to be treated.

33. The compound for use of any one of the items 29 to 32, wherein the at least one compound in step (b) is selected from the group consisting of chemotherapeutic platinum compounds such as cis-platin, carboplatin and oxaliplatin.

34. A method of treating ovarian cancer in a patient suffering from ovarian cancer, comprising the steps
  (a) providing an ovarian cancer or cancer precursor cell organoid culture from said patient,
  (b) contacting at least one compound with the organoid culture provided in step (a), said at least one compound being selected from active agents suitable for the treatment of ovarian cancer, (c) determining growth or/and propagation of the organoid culture after being contacted with the at least one compound,
  (d) selecting a compound which inhibits growth or/and propagation of the organoid culture, as determined in step (c), and
  (e) treating the patient with compound selected in step (d).

35. Use of an organoid culture of ovarian cancer or cancer precursor cells for determining the efficacy of immune cells in the treatment of ovarian cancer, wherein the immune cells are derived from the patient to be treated or from a heterologous source.

In other preferred embodiments, the present invention is defined by the following items:

1. A method for the production of an ovarian cancer or cancer precursor cell culture, said method comprising the steps:
  (a) cultivating ovarian cancer or cancer precursor cells in a suitable cell culture medium which is capable of BMP signaling, and
  (b) optionally obtaining a cell culture from the cultivation step (a).

2. The method of item 1, wherein the cell culture is an organoid culture.

3. The method of item 1 or 2, wherein the culture medium comprises at least one compound which stimulates BMP signaling selected from mitogenic growth factors such as EGF or/and FGF, a BMP, e.g. BMP2, or/and a Rspondin, e.g. Rspondin1, wherein the medium particularly comprises
  (i) EGF or/and a BMP, or
  (ii) EGF, FGF or/and a Rspondin.

4. The method of any one of items 1 to 3, wherein the culture medium is free from exogenously added Wnt protein, e.g. from an exogenously added Wnt3a protein.

5. The method of any one of items 1 to 4, wherein the culture medium is free of an exogenously added compound which inhibits BMP signaling, such as Noggin.

6. The method of any one of the items 1 to 5, wherein the ovarian cancer cells are primary ovarian cancer or cancer precursor cells, more particularly primary ovarian cancer or cancer precursor cells derived from a human patient.

7. The method of any one of the items 1 to 6, wherein the ovarian cancer is a high-grade serous ovarian carcinoma.

8. An ovarian cancer or cancer precursor cell organoid culture which can be stably propagated.

9. The organoid culture of item 8, as obtainable by the method of any one of items 1 to 7.

10. A biobank, comprising a plurality of different organoid cultures of item 8 or 9.

11. Use of an organoid culture of item 8 or 9, or a biobank of item 10,
  (i) for the determination of the efficacy of a compound in the treatment of ovarian cancer, or
  (ii) for the identification of a compound suitable in the treatment of ovarian cancer.

12. Use of a cell culture medium which is capable of BMP signaling, for the production of a culture, e.g. an organoid culture from ovarian cancer or cancer precursor cells.

13. A method for the determination of the efficacy of a compound in the treatment of ovarian cancer, particularly of ovarian cancer in an individual patient, comprising the steps (a) providing an ovarian cancer or cancer precursor cell organoid culture, (b) contacting at least one compound with the organoid culture provided in step (a), said at least one compound being selected from therapeutically active agents suitable for the treatment of ovarian cancer, (c) determining growth or/and propagation of the organoid culture after being contacted with the at least one compound, and (d) selecting at least one compound which inhibits growth or/and propagation of the organoid culture, as determined in step (c).

14. A screening method for the identification of a compound suitable in the treatment of ovarian cancer, particularly of ovarian cancer in a plurality of different patients, comprising the steps (a) providing at least one ovarian cancer or cancer precursor cell organoid culture, (b) contacting at least one compound with the at least one organoid culture provided in step (a), said at least one compound being selected from candidate active agents presumed to be suitable for the treatment of ovarian cancer, (c) determining growth or/and propagation of the at least one organoid culture after being contacted with the at least one compound, and (d) selecting at least one compound which inhibits growth or/and propagation of at least one organoid culture, as determined in step (c).

15. A compound selected from active agents suitable for the treatment of ovarian cancer, for use in the treatment of a patient suffering from ovarian cancer, said treatment comprising the steps (a) providing an ovarian cancer or cancer precursor cell organoid culture from said patient, (b) contacting at least one compound with the organoid culture provided in step (a), said at least one compound being selected from active agents suitable for the treatment of ovarian cancer, (c) determining growth or/and propagation of the organoid after being contacted with the at least one compound, (d) selecting a compound which inhibits growth or/and propagation of the organoid culture, as determined in step (c), and (e) treating the patient.

In yet other preferred embodiments, the present invention is defined by the following items:

1. A method for the production of an ovarian cancer or cancer precursor cell culture, said method comprising the steps:

(a) cultivating ovarian cancer or cancer precursor cells in a suitable cell culture medium which comprises at least one compound which stimulates BMP signaling, e.g. via BMP2, and (b) optionally obtaining a cell culture from the cultivation step (a).

2. The method of Item 1, wherein the cell culture is an organoid culture.

3. The method of Item 1 or 2, wherein the culture medium is free of Noggin.

4. The method of any one of the Items 1 to 3, wherein the culture medium comprises at least one compound which stimulates Wnt signaling, e.g. via Rspondin 1, 5. The method of any one of the Items 1 to 4, wherein the culture medium comprises at least one compound selected from EGF and FGF.

6. A method for the production of an ovarian cancer or cancer precursor cell culture, said method comprising the steps:

(a) cultivating ovarian cancer or cancer precursor cells in a suitable cell culture medium which is capable of BMP signaling, and (b) optionally obtaining a cell culture from the cultivation step (a), wherein the culture medium comprises (i) at least one compound which stimulates BMP signaling, e.g. via BMP2, or/and (ii) at least one compound which stimulates Wnt signaling, e.g. via Rspondin 1, and optionally wherein the culture medium comprises at least one compound selected from EGF and FGF, and wherein the culture medium is free of Noggin, and wherein the cell culture is an organoid culture.

7. A method for the production of an ovarian cancer or cancer precursor cell culture, said method comprising the steps:

(a) cultivating ovarian cancer or cancer precursor cells in a suitable cell culture medium, wherein the culture medium comprises (i) at least one compound which stimulates BMP signaling, e.g. via BMP2, or/and (ii) at least one compound which stimulates Wnt signaling, e.g. via Rspondin1, and optionally wherein the culture medium comprises at least one compound selected from EGF and FGF, and wherein the culture medium is free of Noggin, and (b) optionally obtaining a cell culture from the cultivation step (a), and wherein the cell culture is an organoid culture.

8. The method of any one of the items 1 to 7, wherein the medium comprises (iii) EGF and a BMP, or (iv) EGF, FGF and a Rspondin.

9. The method of any one of items 1 to 8, wherein the culture medium is free from exogenously added Wnt protein, e.g. from an exogenously added Wnt3a protein.

10. The method of any one of items 1 to 9, wherein the culture medium is free of an exogenously added compound which inhibits BMP signaling.

11. The method of any one of the items 1 to 10, wherein the ovarian cancer cells are primary ovarian cancer or cancer precursor cells, more particularly primary ovarian cancer or cancer precursor cells derived from a human patient.

12. The method of any one of the items 1 to 11, wherein the ovarian cancer is a high-grade serous ovarian carcinoma.

13. An ovarian cancer or cancer precursor cell organoid culture which can be stably propagated.

14. The organoid culture of item 13, as obtainable by the method of any one of items 1 to 12.

15. A biobank, comprising a plurality of different organoid cultures of item 13 or 14.

16. Use of an organoid culture of item 13 or 14, or a biobank of item 15, (i) for the determination of the efficacy of a compound in the treatment of ovarian cancer, or (ii) for the identification of a compound suitable in the treatment of ovarian cancer.

17. Use of a cell culture medium for the production of a culture from ovarian cancer or cancer precursor cells, e.g. an organoid culture, wherein the culture medium comprises
   (i) at least one compound which stimulates BMP signaling, e.g. via BMP2, or/and
   (ii) at least one compound which stimulates Wnt signaling, e.g. via Rspondin1, and
   optionally wherein the culture medium comprises at least one compound selected from EGF and FGF, and
   wherein the culture medium is free of Noggin.

18. Use of a cell culture medium which is capable of BMP signaling, for the production of a culture from ovarian cancer or cancer precursor cells, e.g. an organoid culture, wherein the culture medium comprises
   (i) at least one compound which stimulates BMP signaling, e.g. via BMP2, or/and
   (i) at least one compound which stimulates Wnt signaling, e.g. via Rspondin1, and
   optionally wherein the culture medium comprises at least one compound selected from EGF and FGF, and
   wherein the culture medium is free of Noggin.

19. A method for the determination of the efficacy of a compound in the treatment of ovarian cancer, particularly of ovarian cancer in an individual patient, comprising the steps
   (a) providing an ovarian cancer or cancer precursor cell organoid culture according to item 13 or 14,
   (b) contacting at least one compound with the organoid culture provided in step (a), said at least one compound being selected from therapeutically active agents suitable for the treatment of ovarian cancer,
   (c) determining growth or/and propagation of the organoid culture after being contacted with the at least one compound, and
   (d) selecting at least one compound which inhibits growth or/and propagation of the organoid culture, as determined in step (c).

20. A screening method for the identification of a compound suitable in the treatment of ovarian cancer, particularly of ovarian cancer in a plurality of different patients, comprising the steps
   (a) providing at least one ovarian cancer or cancer precursor cell organoid culture according to item 13 or 14,
   (b) contacting at least one compound with the at least one organoid culture provided in step (a), said at least one compound being selected from candidate active agents presumed to be suitable for the treatment of ovarian cancer,
   (c) determining growth or/and propagation of the at least one organoid culture after being contacted with the at least one compound, and
   (d) selecting at least one compound which inhibits growth or/and propagation of at least one organoid culture, as determined in step (c).

21. A compound selected from active agents suitable for the treatment of ovarian cancer, for use in a method for the treatment of a patient suffering from ovarian cancer, said method for treatment comprising the steps
   (a) providing an ovarian cancer or cancer precursor cell organoid culture according to item 13 or 14 from said patient,
   (b) contacting at least one compound with the organoid culture provided in step (a), said at least one compound being selected from active agents suitable for the treatment of ovarian cancer,
   (c) determining growth or/and propagation of the organoid after being contacted with the at least one compound,
   (d) selecting a compound which inhibits growth or/and propagation of the organoid culture, as determined in step (c), and
   (e) treating the patient with compound selected in step (d).

A preferred embodiment relates to a method for the production of an ovarian cancer or cancer precursor cell culture, said method comprising the steps:
   (a) cultivating ovarian cancer or cancer precursor cells in a suitable cell culture medium which comprises at least one compound which stimulates BMP signaling, e.g. via BMP2, and
   (b) optionally obtaining a cell culture from the cultivation step (a),
   wherein the cell culture is an organoid culture, and wherein the culture medium is free of Noggin.

Another preferred embodiment relates to a method for the production of an ovarian cancer or cancer precursor cell culture, said method comprising the steps:
   (a) cultivating ovarian cancer or cancer precursor cells in a suitable cell culture medium which comprises (i) at least one compound which stimulates BMP signaling, e.g. via BMP2, or/and (ii) at least one compound which stimulates Wnt signaling, e.g. via Rspondin 1, and
   (b) optionally obtaining a cell culture from the cultivation step (a),
   wherein the cell culture is an organoid culture, and wherein the culture medium is free of Noggin.

Yet another preferred embodiment relates to a method for the production of an ovarian cancer or cancer precursor cell culture, said method comprising the steps:
   (a) cultivating ovarian cancer or cancer precursor cells in a suitable cell culture medium which comprises (i) at least one compound which stimulates BMP signaling, e.g. via BMP2, or/and (ii) at least one compound which stimulates Wnt signaling, e.g. via Rspondin 1,
   (b) optionally obtaining a cell culture from the cultivation step (a),
   wherein the cell culture is an organoid culture, and wherein the culture medium is free of Noggin, and wherein the culture medium comprises at least one compound selected from EGF and FGF.

Further, the present invention shall be explained in more detail by the following Figures and Examples.

FIGURE LEGENDS

FIG. 1: Example of an ovarian cancer cell organoid culture line (OVK ORG 11) which grows in medium A Although some cell aggregates were initially formed in the SM standard medium, the culture underwent growth arrest in the next passage. Organoids cultivated in medium A reached much bigger size (~200-500 µm) and could be propagated stably.

Figure 2:
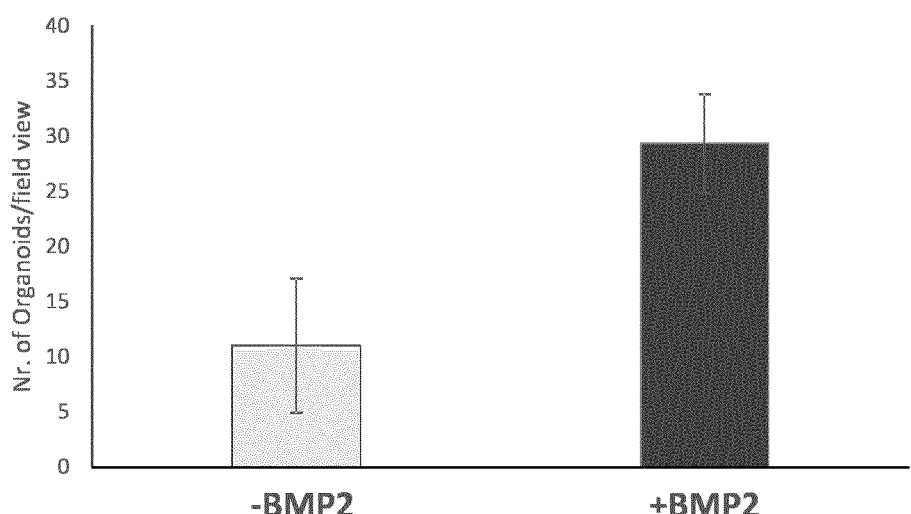

FIG. 2: Addition of soluble BMP2 improves organoid growth in high-grade serous carcinoma (HGSC) 3D cultures The plot is representative of formed organoid counts per field view from 3 different patient isolates which were cultivated in parallel in medium−/+BMP2.

Figure 3:
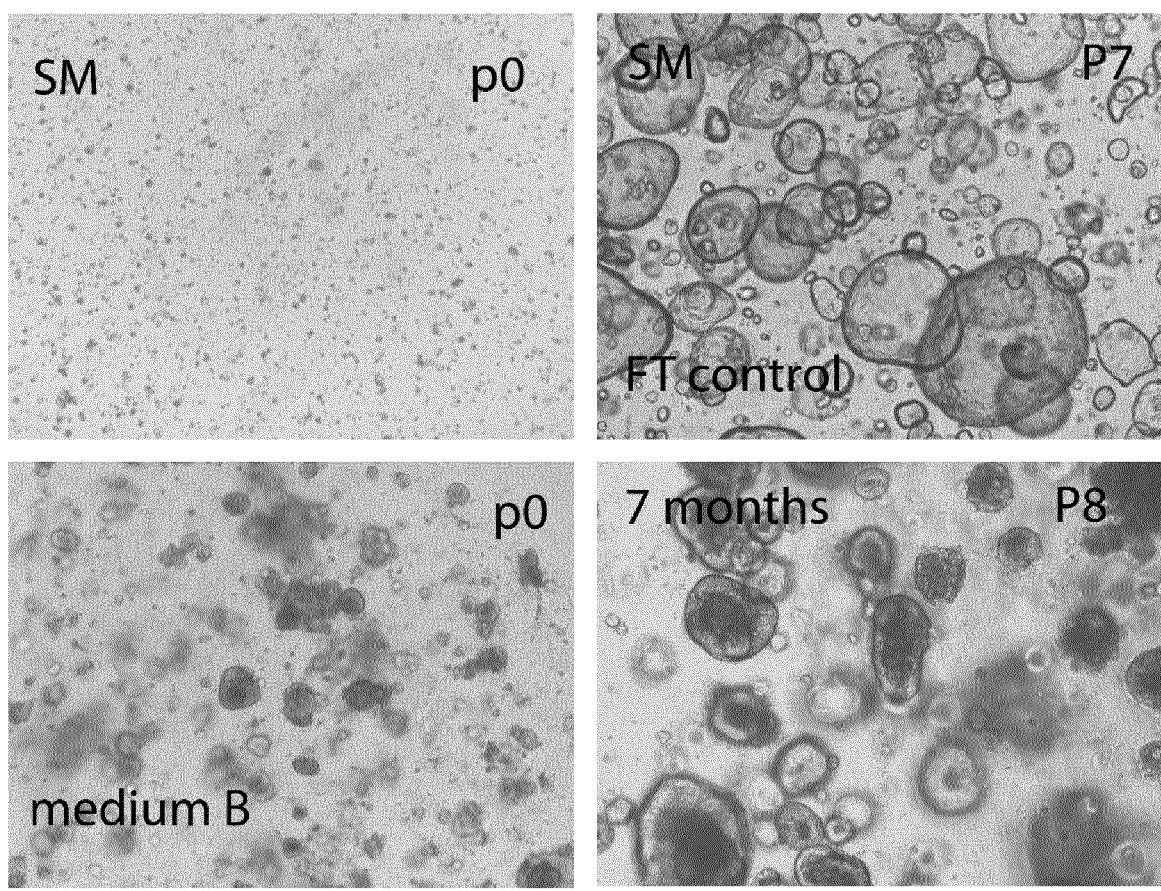

FIG. 3: Patient-derived organoid cell line (OVK ORG 2) shows established stable long term growth in medium B The upper part shows the absence of organoid formation from cancer cells in standard SM medium, while healthy fallopian tube cells from the same patient gave rise to a stable organoid culture. The lower part shows the formation of organoids from cancer cells in medium B.

Figure 4:
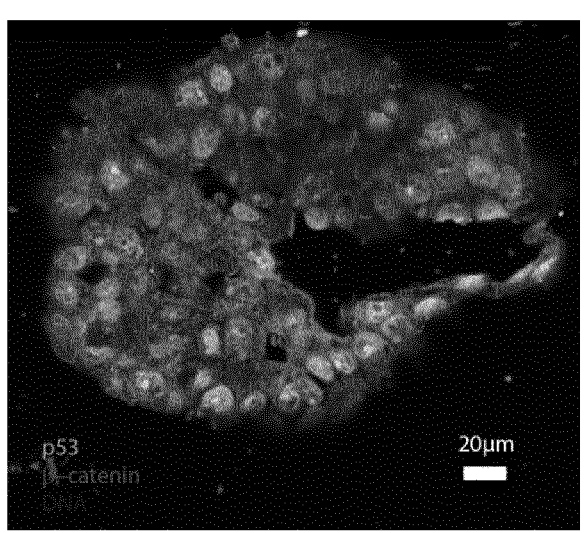
Figure 4:
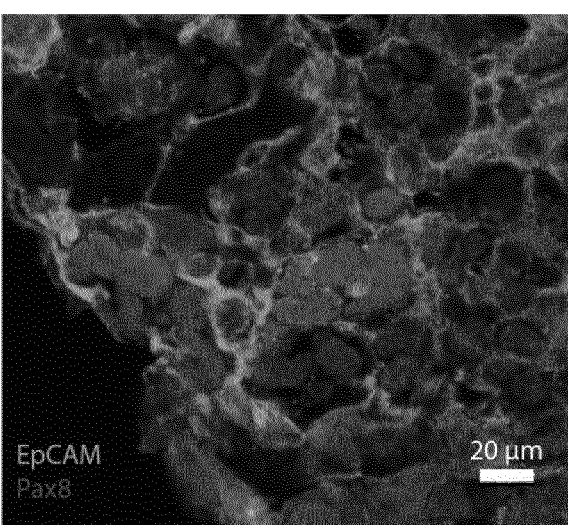

FIG. 4: Confocal images of a patient derived organoid cell line (OVK ORG 11) showing strong nuclear accumulation of p53 which is characteristic in cells harboring p53.

Organoids are positive for p53, EpCAM and PAX8 and have highly polymorphic nuclei which is hallmark of HGSC.

Figure 5:
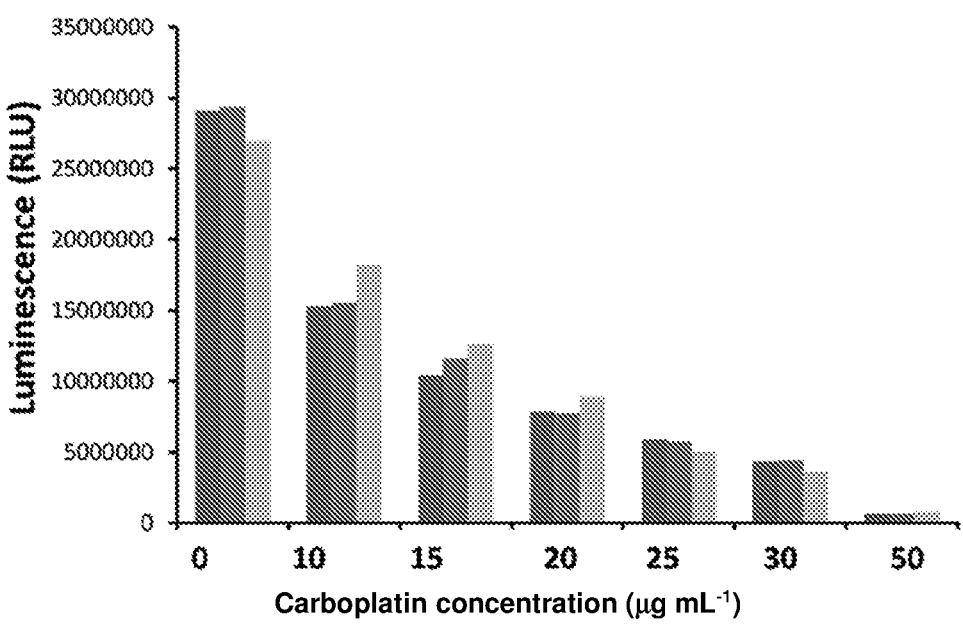
Figure 5:
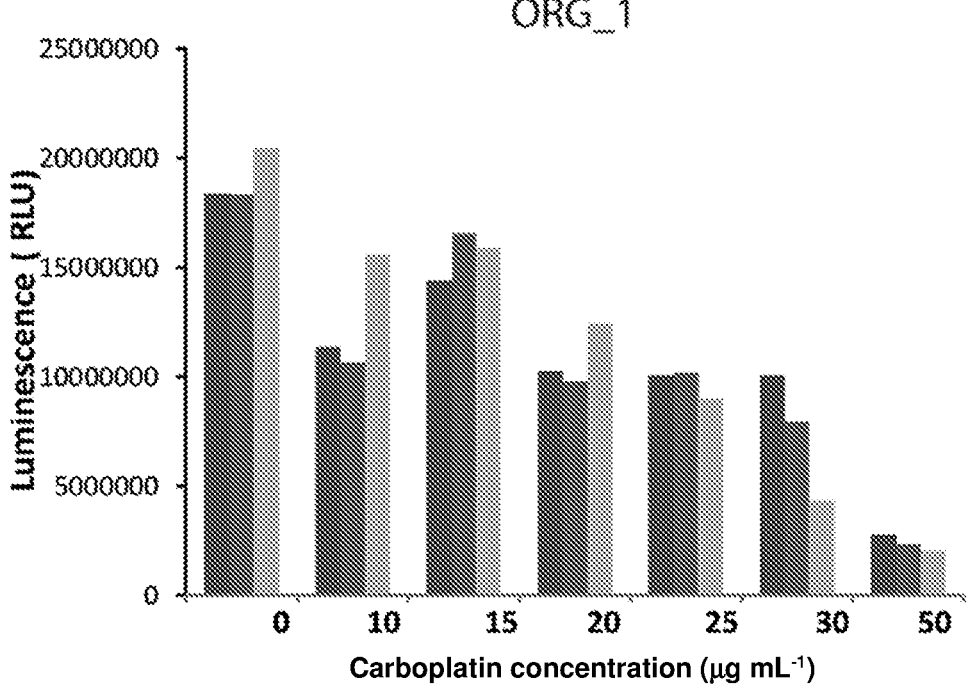

FIG. 5: Individual response curve to carboplatin treatment in organoid cell lines ORG1 and ORG2

Treatment of organoid cancer lines with carboplatin, a standard component of the chemotherapy treatment for HGS patients revealed differences in responsivness and kinetics. Cell vialiability (y axis) was determined proportional to the strength of luminiscence signal (Cell Titer® Glow 3D Promega). The test also showed only minor technical variability among triplicates (bars of different color) which makes it suitable for quantitative studies.

EXAMPLE

Methods

All samples processed in the study were obtained as fragments of solid tumor deposits from chemotherapy naïve high grade serous ovarian cancer (HGSC) patients undergoing debulking surgery. Tumor samples were removed during the surgery. Initial assessment of the tumor content was performed by the operating clinician. Samples were transported on ice within 2 hours of the procedure and subjected to a cell isolation procedure.

The following steps were performed to ensure proper quality analysis (phenotypic and genotypic) of the processed tissue:—a 3 mm$^3$ fragment was shock frozen in liquid nitrogen and stored at −80° C.; a further 3 mm$^3$ fragment was fixed at room temperature (RT) for 24 h in 3.7% paraformaldehyde (PFA) followed by paraffin embedding. The remaining tissue was used for cell isolation.

In the following, an experimental procedure including all the steps required for establishment of long term organoid culture from HGSC patients tissue is described. As Matrigel® is highly selective and supports growth of epithelial cells no absolute exclusion of stroma cells is necessary to obtain pure organoid lines which are 100% EpCam positive.

Step 1: Isolation and 2D Cultivation of Cancer Cells

Adv. +++: Advanced F12 Medium+HEPES (6 ml)+Glutamax (5 ml)+5% fetal calf serum (FCS)

Adv. ++: Advanced F12 Medium+HEPES (6 ml)+Glutamax (5 ml)

Cut tissue with a scissor in small pieces and then mince further with scalpel for 3-5 minutes Collect all fragments, incubate with 2 ml Collagenase Type 1+2 ml Collagenase type II and transfer to a 6 well plate, Incubate fragments for 45 min at 37° C. 5% CO$_2$, Add 5 ml Adv +++ and transfer in to a 50 ml Falcon tube, Vortex vigorously for 30 seconds, Let pieces settle down, take supernatant and transfer in to a fresh tube, Add again 5 ml Adv +++, mix with a pipette, Let pieces settle down, take supernatant and transfer in to a fresh tube, Centrifuge for 5 min at 400 rpm, Discard supernatant, Prepare 10 ml Adv +++, add 30 μl Y-27632 and 10 μl hEGF (final conc. 10 ng/ml), Resuspend cell pellet in medium, Seed cell in a flask, Incubate at 5% CO$_2$ at 37° C. and grow cells 3-5 days prior to transfer to 3D culture.

Step 2: Seeding Cancer Cells in 3D Culture

Remove Medium from the flask and wash one time with PBS,

Add 1 ml TrypLE and incubate 10 min until cells are completely detached,

Remove cells with 5 to 10 ml of Adv ++ and transfer in a 15 ml Falcon tube,

Centrifuge at 1200 rpm for 5 min,

Remove supernatant,

Add 1 ml add Adv ++ and count cells,

Keep cells on ice during this time;

Seeding of Cells:

For a 24 well plate—20,000 cells per 50 μl Matrigel

For a 48 well plate—10,000 cells per 25 μl Matrigel

Seed cells in prewarmed plate,

Let Matrigel solidify for 30 min in the incubator,

Add growth medium,

For a 24 well plate—500 μl,

For a 48 well plate—250 μl,

Change Medium twice times per week.

Step 3: Splitting of the Cancer Organoid Culture

Splitting should be carried out about once per 3 weeks.

Remove medium from all wells,

Add 1 ml ice cold Adv +++ to the Matrigel droplet,

Scrape with pipet tip on the bottom of well,

As Matrigel dissolves transfer organoids in the medium to 15 ml Falcon tube,

Wash the splitting well with 500 μl cold medium and put the medium thereafter into the same Falcon tube, Fill up to 5 ml with Adv ++ (cold) and spin down (1000 rpm, 5 min), Remove supernatant and add 1 ml TrypLE, Incubate for 10 min at 37 C, vortex shortly 2-3 times for 20 seconds, Fill up to 5 ml with cold Adv ++, Centrifuge at 4° C. for 5 min at 1200 rpm, Remove the supernatant, If impossible, wash the pellet again, For 1 well dissolve cells in 50 μl Matrigel, seed as an drop per well, Incubate for 30 min at 37° C., Add culture medium, Change medium every 3-4 days.

Results

We report culture conditions and procedures for establishing a stable long term organoid culture from primary tumor deposits of high grade serous ovarian cancer.

There are substantial changes in the niche conditions which need to be provided to ensure in vitro cultivation of patient tumor samples, compared to the already described niche conditions for adult stem cells from the healthy epithelium (Kessler et al., 2015, supra). Significantly, we found that exogenous supplementation of Wnt 3a is detrimental for ovarian cancer stem cells as all of the established lines grew in Wnt3a-negative media. However, some individual samples continued to benefit from supplementation of Wnt agonist.

In contrast to the healthy oviductal epithelium, and other healthy mucosal models, we found that a HGSC organoid culture is dependent on active BMP signaling. This may be achieved by omission of the Noggin from the media (see medium A). As Noggin is a potent chelating agent for endogenous BMPs which are produced in the organoids this leads to the activation of downstream BMP signaling. Interestingly, none of the tested cancer tissues was able to give rise to an organoid culture in standard 3D medium (SM). Organoids could not form at all, or experienced growth arrest during cultivation (FIG. 1).

Cancer cells seeded in medium A, containing only basic medium components plus EGF and BMP2, gave rise to a stable and expandable long term culture. Although endogenous activation of the BMP pathway occurs as direct consequence of the absence of Noggin in the medium it was tested if increasing the amount of BMP confers further growth advantage to the organoids. Indeed, organoid formation efficiency in the HGSC organoid cultures was clearly improved by exogenous supplementation of soluble BMP2 (final concentration 10 ng/ml) to the growth medium (FIG. 2). Thus, BMP2 was included in the standard composition of the medium A.

We found stable long term propagation of HGSC organoids in basic medium (see table) supplemented solely with EGF and BMP2 (designated medium A). However two of the generated cultures required additional growth support which was provided by Rspondin 1 and FGF (medium B) in the medium. Both media lack Noggin and thus have activated BMP signaling contrary to the requirements of a healthy organoid culture. As a control comparison, a Fallopian tube organoid culture from the same patient efficiently cultivated in SM medium, showing that new properties are restricted to the malignant tissue.

TABLE 1

| Basic components (present in all media) | Components of standard medium for healthy FT (SM) | Components of medium A | Components of medium B |
|---|---|---|---|
| Advance F12++, B27 2%, Nicotinamide 1 mM, N2 1%, Y-27632 9 μM, TGFβ RI 0.5 μM inhibitor | EGF 10ng/ ml, FGF 100 ng/ml, Noggin 100 ng/ml, Rspondin 10% conditioned medium Wnt 25% conditioned medium | EGF 10 ng/ml, BMP2 10 ng/ml | EGF 10 ng/ml, FGF 100 ng/ml, Rspondin, 10% conditioned medium |

In order to find out whether Rspondin is required for achieving stable long term cultivation, each patient sample should be subjected to parallel testing under two different conditions in the presence and absence of Rspondin: for example, medium A and (general organoid culture supplements+BMP2+EGF) and medium B (general organoid culture supplements+EGF+FGF+Rspondin1).

Patient-derived organoid cultures from ovarian cancer can be propagated stably in a long term culture (>6 months) with regular splitting intervals of e.g. 3-4 weeks. The cultures can be routinely frozen and thawed which is a key prerequisite for biobanking storage.

Immunofluorescence analysis of the key structural and functional biomarkers confirmed that organoids match native tumor tissue in phenotype, e.g. PAX8 confirming Mullerean lineage, EpCAM, p53 and p16 (FIG. 4). All tested organoid cultures were matched in phenotype to the fragment of native tumor processed and stained in standard procedure which was used for clinical diagnosis. Ovarian cancer cancer organoids mostly lack central cavities in contrast to fallopian tube organoids which are built of polarized epithelial monolayers. This is expected as histological atypia and stratification are present already in the early stages of the carcinogenesis in the fallopian tube (Shaw et al 2009, Modern Pathology 22, 1135-1138). Panel sequencing of paired organoid culture and tissue confirmed that the tested organoids recapitulate cancer tissue composition also on the genomic level. Importantly cultures can be expanded to multi-well format to enable high throughput experimental set up. Pilot drug test experiments with carboplatin, first line compulsory agent in the treatment of the HGSC patients revealed that organoids show individual patient profiles in their response to the drug which can be determined by precise quantitative measurements.

Therefore it can be concluded that ovarian cancer organoids fatefully reproduce tumor cells in vitro and thus represent an adequate biological model which opens a potential to advance treatment approaches in several major categories: 1) in vitro testing of drug response (complementary to the in silico predictions based on NGS data); 2) drug screening of new drug candidates; 3) in vitro study of resistance mechanisms; 4) identification of new biomarkers, as tissue based approaches are limited by a high background due to complexity of in vivo system; 5) identification of novel neo-antigens for improving efficiency of immunotherapies; 6) development of assays to study antigen specific immune responses in vitro such are direct cytotoxicity assays (CTL assays) by using patient cancer organoids; 7) investigating mechanisms to improve efficiency of the immunotherapy by genetically modifying cancer organoids.

Within this study we have so far generated 15 patient organoid lines. The production method could be further improved by optimizing clinical sampling during surgery as most of the patients undergo surgery at FIGO (International Federation of Gynecology and Obstetrics) stage Ill where metastatic peritoneum deposits are abundant and any large tumor mass is likely heterogeneous. The procedure described herein sets a major milestone which enables creation of live tumor biobanks for high number of patients.

Taking into account very narrow therapeutic options which are currently available to ovarian cancer patients, and wide spread platinum resistance which ultimately develops in all patients, the organoid culture represents an attractive model to test in advance the therapeutic response of each patient to different classes of approved drugs and provide the clinician with valuable information which could improve decision making process at the late stages. This type of application is a promising methodology for improvement of personalized therapy.

The invention claimed is:

1. A method for the production of an ovarian cancer or cancer precursor cell organoid culture, said method comprising:
(a) isolating ovarian cancer or cancer precursor cells obtained from a human patient with ovarian carcinoma,
(b) cultivating said ovarian cancer or cancer precursor cells in a cell culture medium, wherein:
the cell culture medium comprises at least one compound which stimulates Bone Morphogenetic Protein (BMP) signaling and at least one compound selected from the group consisting of a serum-free neuronal supplement, nicotine amide, a ROCK inhibitor, an N-2 supplement and a TGF β inhibitor, and
the cell culture medium:
(i) is free of Noggin and free from exogenously added Wnt protein, and comprises EGF at a concentration of about 1-200 ng/ml and BMP2 at a concentration of about 1-50 ng/ml, or (ii) is free of Noggin and free from exogenously added Wnt protein, and comprises EGF at a concentration of about 1-200 ng/ml, FGF at a concentration of about 20-500 ng/ml, and Rspondin at a concentration of about 50-100 ng/ml, and (c) obtaining an organoid cell culture from the cultivation step (b), and (d) culturing said organoid cell culture.

2. The method of claim 1, wherein the cell culture medium is free of an exogenously added compound which inhibits BMP signaling.

3. The method of claim 1, wherein the ovarian cancer cells are primary ovarian cancer.

4. The method of claim 1, wherein the ovarian cancer is a high-grade serous ovarian carcinoma.

5. The method of claim 1, wherein Rspondin is Rspondin1.

6. The method of claim 1, wherein the cell culture medium is free from an exogenously added Wnt3a protein.

7. The method of claim 1, wherein the ROCK inhibitor is Y-27632.

8. The method of claim 1, wherein the TGF β inhibitor is SB-431542.

9. The method of claim 1, wherein the culturing is for at least six months.

\*　\*　\*　\*　\*